United States Patent
Ito et al.

(10) Patent No.: US 9,499,644 B2
(45) Date of Patent: Nov. 22, 2016

(54) PRODUCTION METHOD OF POLAR GROUP-CONTAINING OLEFIN POLYMERS

(71) Applicants: THE UNIVERSITY OF TOKYO, Tokyo (JP); SHOWA DENKO K.K., Tokyo (JP)

(72) Inventors: Shingo Ito, Tokyo (JP); Kyoko Nozaki, Tokyo (JP); Yusuke Ota, Tokyo (JP); Yoshikuni Okumura, Oita (JP); Junichi Kuroda, Oita (JP)

(73) Assignees: SHOWA DENKO K.K., Tokyo (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 14/762,598

(22) PCT Filed: Jan. 22, 2014

(86) PCT No.: PCT/JP2014/051872
§ 371 (c)(1),
(2) Date: Jul. 22, 2015

(87) PCT Pub. No.: WO2014/115895
PCT Pub. Date: Jul. 31, 2014

(65) Prior Publication Data
US 2015/0368376 A1     Dec. 24, 2015

(30) Foreign Application Priority Data

Jan. 23, 2013 (JP) .................. 2013-010226
May 10, 2013 (JP) .................. 2013-099944

(51) Int. Cl.
| | |
|---|---|
| *C07F 15/04* | (2006.01) |
| *C08F 4/80* | (2006.01) |
| *C08F 220/02* | (2006.01) |
| *C08F 10/00* | (2006.01) |
| *C08F 10/02* | (2006.01) |
| *C08F 4/60* | (2006.01) |
| *C07F 9/54* | (2006.01) |
| *C07F 15/00* | (2006.01) |

(52) U.S. Cl.
CPC ............. *C08F 10/02* (2013.01); *C07F 9/5442* (2013.01); *C07F 15/006* (2013.01); *C07F 15/0066* (2013.01); *C08F 4/60031* (2013.01); *C08F 4/80* (2013.01); *C08F 220/02* (2013.01)

(58) Field of Classification Search
CPC ...... C07F 15/06; C08F 4/60031; C08F 4/80; C08F 210/00; C08F 216/00; C08F 10/00; C08F 220/02
See application file for complete search history.

(56) References Cited

U.S. PATENT DOCUMENTS

2012/0116036 A1    5/2012   Nozaki et al.

FOREIGN PATENT DOCUMENTS

| CN | 102498137 A | 6/2012 |
|---|---|---|
| EP | 1 964 862 A1 | 9/2008 |
| EP | 2 351 761 A1 | 8/2011 |
| JP | 2011-68881 A | 4/2011 |
| WO | 2011/025053 A2 | 3/2011 |

OTHER PUBLICATIONS

Shingo Ito, et al., "Coordination—Insertion Copolymerization of Allyl Monomers with Ethylene", Journal of the American Chemical Society, 2011, pp. 1232-1235, vol. 133.
International Search Report for PCT/JP2014/051872 dated Mar. 19, 2014 [PCT/ISA/210].
Written Opinion for PCT/JP2014/051872 dated Mar. 19, 2014 [PCT/ISA/237].

*Primary Examiner* — Caixia Lu
(74) *Attorney, Agent, or Firm* — Sughrue Mion, PLLC

(57) ABSTRACT

The present invention relates to a method for producing a homopolymer of olefin represented by formula (1): $CH_2=CHR^1$ ($R^1$ is a hydrogen atom or hydrocarbon group having 1 to 20 carbon atoms) or a copolymer of two or more thereof or a method for producing a copolymer of olefin represented by formula (1) with olefin containing a polar group represented by formula (2): $CH_2=CHR^2R^3$ ($R^2$ is a hydrogen atom or methyl group, $R^3$ is $-COOR^{12}$, $-CN$, $-OCOR^{12}$, $-OR^{12}$, $-CH_2-OCOR^{12}$, $-CH_2OH$, $-CH_2-N(R^{13})_2$ or $-CH_2-Hal$ ($R^{12}$, $R^{13}$ and Hal have the same meanings as stated in the description), using as a catalyst a metal complex of group 10 elements in the periodic system typified by the structure represented by formula 1 ("Men" represents a menthyl group and "Me" represents a methyl group). The present invention enables the production of high molecular weight polymers of the polar group-containing monomers such as polar group-containing allyl compounds.

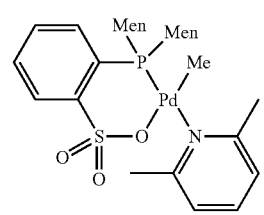

19 Claims, No Drawings

PRODUCTION METHOD OF POLAR GROUP-CONTAINING OLEFIN POLYMERS

CROSS REFERENCE TO RELATED APPLICATIONS

This application is a National Stage of International Application No. PCT/JP2014/051872, filed on Jan. 22, 2014 (which claims priority from Japanese Patent Application Nos. 2013-010226, filed on Jan. 23, 2013, and 2013-099944, filed on May 10, 2013), the contents of which are incorporated herein by reference in their entirety.

TECHNICAL FIELD

The present invention relates to a method for producing olefin polymers, specifically a method for producing polymers of polar group-containing monomers such as a polar group-containing allyl compound and the like.

BACKGROUND ART

Copolymers of olefin such as ethylene and propylene which is a nonpolar monomer and a vinyl monomer containing polar group have been widely known.

Specifically, ethylene-vinyl alcohol copolymers (EVOH) are random copolymer comprising ethylene and vinyl alcohol and synthesized by saponifying ethylene-vinyl acetate copolymers obtained by radical copolymerization of ethylene and vinyl acetate. EVOH is used in a wide range of fields for purposes such as food packages by taking advantage of its excellent gas barrier property.

The polymerization of monomers containing allyl group is more difficult compared to that of vinyl monomers, and the polymer of allyl group-containing monomers has been almost unheard. The main reason for this is that when allyl group-containing monomers are subjected to radical polymerization, the polymer propagation reaction proceeds very slowly due to the degenerative chain transfer reaction to monomers and hence only oligomers having low degree of polymerization can be obtained (Chem. Rev. 58, 808 (1958)).

JP-A-2011-68881 (International Publication No. WO 2011/025053; Patent Document 1) and J. Am. Chem. Soc., 133, 1232 (2011) (Non-patent Document 1) disclose coordination copolymerization of ethylene and polar group-containing allyl monomers using a catalyst of metal complex of group 10 elements in the periodic system, and polymers of polar group-containing allyl monomers are synthesized, which have not been obtained by a radical polymerization method. However, the molecular weight of the obtained polymer was about several thousands to several tens of thousands and there was room for development in terms of film formability and transparency.

PRIOR ART

Patent Document

[Patent Document 1] JP-A-2011-68881 (WO 2011/025053)

Non-Patent Document

[Non-patent Document 1] J. Am. Chem. Soc., 133, 1232 (2011)

SUMMARY OF THE INVENTION

Problems to be Solved by the Invention

An objective of the present invention is to provide a method for producing a high molecular weight olefin copolymer containing polar group, which copolymer is available for various applications.

Means to Solve the Problem

As a result of intensive studies to solve the above-mentioned problem, the present inventors have found that a high molecular weight copolymer of polar group-containing vinyl monomers, which copolymer is available for various applications, can be provided by polymerizing polar group-containing vinyl monomers (including polar group-containing allyl monomers) using a novel metal complex of group 10 elements as a catalyst, and accomplished the present invention based on this finding.

That is, the present invention relates to the method for producing polymers in [1] to [17] and a compound in [18] described below:

[1] A method for producing a homopolymer or copolymer of monomers comprising olefin represented by formula (1)

$$CH_2=CHR^1 \quad (1)$$

(in the formula, $R^1$ represents a hydrogen atom or hydrocarbon group having 1 to 20 carbon atoms) using as a polymerization catalyst a metal complex represented by formula (C1)

(in the formula, M represents a metal atom of group 10 element in the periodic system; X represents a phosphorous atom (P) or an arsenic atom (As); $R^5$ represents a hydrogen atom or hydrocarbon group having 1 to 30 carbon atoms which may be substituted by one or more groups selected from a halogen atom, alkoxy group, aryloxy group and acyloxy group; Y, $R^6$ and $R^7$ independently represent a hydrogen atom, alkoxy group, aryloxy group, silyl group, amino group or hydrocarbon group having 1 to 30 carbon atoms which may be substituted by one or more groups selected from a halogen atom, alkoxy group and aryloxy group; and at least one of $R^6$ and $R^7$ represents a cycloalkyl group represented by formula (5)

(in the formula, R represents an alkylene group having 1 to 14 carbon atoms which may have a substituent; $R^9$, $R^{10}$ and $R^{11}$ independently represent a hydrogen atom, alkoxy group, aryloxy group, silyl group, amino group or hydrocarbon group having 1 to 30 carbon atoms which may be substituted by one or more groups selected from a halogen atom, alkoxy group and aryloxy group; at least one of $R^9$ and $R^{10}$ is not a hydrogen atom; $R^9$, $R^{10}$, $R^{11}$ and the above-mentioned alkylene group R may bond to each other to form a ring structure. In the formula, the bond of the carbon atom to X in formula (C1) is also shown);

Q represents a bivalent group indicated in the brackets of Z[—S(=O)$_2$—O-]M, Z[—C(=O)—O-]M, Z[—P(=O)(—OH)—O-]M or Z[—S-]M (Z and M at the beginning and at the end of the formulae are described to show the coupling direction of the groups). Z represents a hydrogen atom or a hydrocarbon group having 1 to 40 carbon atoms which may be substituted by one or more groups selected from a halogen atom, alkoxy group and aryloxy group. Y and Z may bond to each other to form a ring structure. $R^6$ or $R^7$ may bond to Y to form a ring structure. L represents an electron-donating ligand and q is 0, ½, 1 or 2).

[2] The method for producing a polymer as described in [1] above, wherein the copolymer is the copolymer of olefin represented by formula (1)

(in the formula, $R^1$ has the same meaning as described in [1] above) and a polar group-containing olefin represented by formula (2)

(in the formula, $R^2$ represents a hydrogen atom or a methyl group; $R^3$ represents —COOR$^{12}$, —CN, —OCOR$^{12}$, —OR$^{12}$, —CH$_2$—OCOR$^{12}$, —CH$_2$OH, —CH$_2$—N(R$^{13}$)$_2$ or —CH$_2$-Hal ($R^{12}$ represents a hydrogen atom or hydrocarbon group having 1 to 5 carbon atoms; $R^{13}$ represents a hydrogen atom, hydrocarbon group having 1 to 5 carbon atoms, aromatic substituent having 6 to 18 carbon atoms or alkoxy carbonyl group; and Hal represents a halogen atom)).

[3] The method for producing a polymer as described in [1] or [2] above, wherein the number of carbon atoms of the alkylene group R which may have a substituent in formula (5) is 2 to 6.

[4] The method for producing a polymer as described in any one of [1] to [3] above, wherein the number of carbon atoms of the alkylene group R which may have a substituent in formula (5) is 4.

[5] The method for producing a polymer as described in any one of [1] to [4] above, wherein at least one of $R^9$ and $R^{10}$ in formula (5) is an alkyl group having 1 to 6 carbon atoms or cycloalkyl group having 3 to 8 carbon atoms.

[6] The method for producing a polymer as described in any one of [1] to [5] above, wherein at least one of $R^9$ and $R^{10}$ in formula (5) is an isopropyl group.

[7] The method for producing a polymer as described in any one of [1] to [6] above, wherein at least one of $R^6$ and $R^7$ in formula (C1) is 2-isopropyl-5-methylcyclohexyl group (menthyl group) represented by the following formula

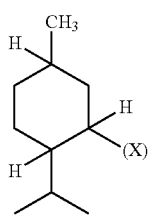

(in the formula, the bond between the carbon atom and X is also shown and X has the same meaning as described in formula (C1)).

[8] The method for producing a polymer as described in any one of [1] to [7] above, wherein both of $R^6$ and $R^7$ in formula (C1) are 2-isopropyl-5-methylcyclohexyl group (menthyl group).

[9] The method for producing a polymer as described in any one of [1] to [8] above, wherein the catalyst represented by formula (C1) is represented by formula (C2)

(in the formula, $Y^1$ represents a halogen atom or bivalent hydrocarbon group having 1 to 70 carbon atoms which may be substituted by one or more groups selected from alkoxy group and aryloxy group; Q, M, X, $R^5$, $R^6$, $R^7$, L and q have the same meaning as described in formula (C1)).

[10] The method for producing a polymer as described in [9] above, wherein Q in formula (C2) is —SO$_2$—O— (provided that S bonds to $Y^1$ and O bonds to M).

[11] The method for producing a polymer as described in [9] or [10] above, wherein the catalyst represented by formula (C2) is represented by formula (C3)

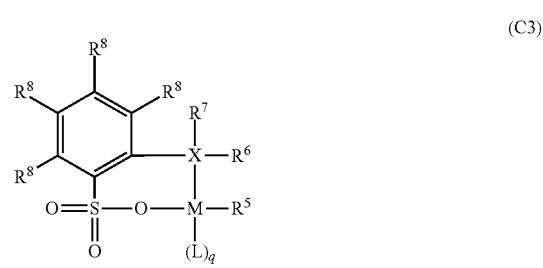

(in the formula, four $R^8$s independently represent a hydrogen atom, alkyl group having 1 to 8 carbon atoms, alkoxy group having 1 to 8 carbon atoms, aryloxy group having 6 to 18 carbon atoms or a halogen atom; and M, X, $R^5$, $R^6$, $R^7$, L and q have the same meanings as described in formula (C1)).

[12] The method for producing a polymer as described in [11] above, wherein all of $R^8$s in formula (C3) are a hydrogen atom.

[13] The method for producing a polymer as described in any one of [1] to [12] above, wherein M is Pd.

[14] The method for producing a polymer as described in any one of [1] to [13] above, wherein X is P.

[15] The method for producing a polymer as described in any one of [1] to [14] above, wherein the olefin represented by formula (1) is ethylene.

[16] The method for producing a polymer as described in any one of [1] to [15] above, wherein the polar group-containing olefin represented by formula (2) is an allyl compound in which $R^3$ represents —CH$_2$—OCOR$^{12}$, —CH$_2$OH, —CH$_2$N—(R$^{13}$)$_2$ or —CH$_2$-Hal ($R^{12}$, $R^{13}$ and Hal have the same meanings as described in formula (2)).

[17] The method for producing a polymer as described in any one of [1] to [16] above, wherein the polar group-containing olefin represented by formula (2) is allyl acetate.

[18] A compound represented by formula (C4)

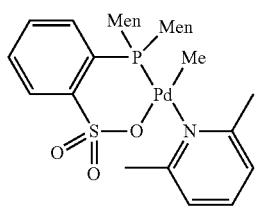

(C4)

(in the formula, Men represents a menthyl group and Me represents a methyl group).

Effects of the Invention

A high molecular weight copolymer containing a polar group can be obtained by the method of the present invention, wherein a polar group-containing olefin comprising a polar group-containing allyl monomer and non-polar olefin are copolymerized using a metal complex of group 10 elements in the periodic system as a catalyst, which copolymer was difficult to obtain by a conventional method.

MODE FOR CARRYING OUT THE INVENTION

[Catalyst]

The (structure of) the catalyst comprising metal complex of group 10 elements in the periodic system used in the present invention is represented by formula (C1).

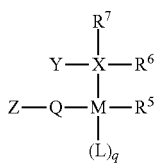

(C1)

(in the formula, M represents a metal atom of group 10 element in the periodic system; X represents a phosphorous atom (P) or an arsenic atom (As); $R^5$ represents a hydrogen atom or hydrocarbon group having 1 to 30 carbon atoms which may be substituted by one or more groups selected from a halogen atom, alkoxy group and aryloxy group; Y, $R^6$ and $R^7$ independently represent a hydrogen atom, alkoxy group, aryloxy group, silyl group, amino group or hydrocarbon group having 1 to 30 carbon atoms which may be substituted by one or more groups selected from a halogen atom, alkoxy group and aryloxy group; and at least one of $R^6$ and $R^7$ represents a cycloalkyl group represented by formula (5)

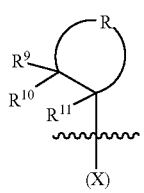

(5)

(in the formula, R represents an alkylene group having 1 to 14 carbon atoms which may have a substituent; $R^9$, $R^{10}$ and $R^{11}$ independently represent a hydrogen atom, alkoxy group, aryloxy group, silyl group, amino group or hydrocarbon group having 1 to 30 carbon atoms which may be substituted by one or more groups selected from a halogen atom, alkoky group and aryloxy group; at least one of $R^9$ and $R^{10}$ is not a hydrogen atom; $R^9$, $R^{10}$, $R^{11}$ and the above-mentioned alkylene group R may bond to each other to form a ring structure. In the formula, the bond of the carbon atom to X in formula (C1) is also shown).

Q represents a bivalent group indicated in the brackets of Z[—S(=O)$_2$—O-]M, Z[—C(=O)—O-]M, Z[—P(=O)(—OH)—O-]M or Z[—S-]M (Z and M at the beginning and at the end of the formulae are described to show the coupling direction of the groups). Z represents a hydrogen atom or a hydrocarbon group having 1 to 40 carbon atoms which may be substituted by one or more groups selected from a halogen atom, alkoxy group and aryloxy group. Y and Z may bond to each other to form a ring structure. $R^6$ and/or $R^7$ may bond to Y to form a ring structure. L represents an electron-donating ligand and q is 0, ½, 1 or 2.

In the present description, the word "hydrocarbon" includes saturated or unsaturated aliphatic hydrocarbon and aromatic hydrocarbon.

The structure of formula (C1) is described below.

M represents an element of group 10 in the periodic system. The elements of group 10 in the periodic system include Ni, Pd and Pt. From the viewpoint of the catalytic activity and molecular weight of the obtained polymers, Ni and Pd are preferable, and Pd is particularly preferable.

X represents a phosphorous (P) atom or an arsenic (As) atom, wherein two electrons coordinate to metal center M. P is preferred as X for reasons of availability and the catalyst cost.

$R^5$ represents a hydrogen atom or a hydrocarbon group having 1 to 30 carbon atoms which may be substituted by one or more group selected from a halogen atom, alkoxy group, aryloxy group and acyloxy group. As the hydrocarbon group having 1 to 30 carbon atoms which may be substituted by one or more group selected from a halogen atom, alkoxy group, aryloxy group and acyloxy group, preferred is an alkyl group having 1 to 6 carbon atoms. The halogen atom is preferably chlorine or bromine. The alkoxy group is preferably methoxy group and ethoxy group. The aryloxy group is preferably phenoxy group. The acyloxy group is preferably acetoxy group and pivaloxy group. Examples of the particularly preferable $R^5$ include a hydrogen atom, methyl group, ethyl group, n-propyl group, iso-propyl group, methoxymethyl group, phenoxymethyl group, 1-acetoxyphenyl group and 1-pivaloxypropyl group.

Y, $R^6$ and $R^7$ each independently represent a hydrogen atom, alkoxy group, aryloxy group, silyl group, amino group, or a hydrocarbon group having 1 to 30 carbon atoms which may be substituted by one or more groups selected from a halogen atom, alkoxy group and aryloxy group; and at least one of $R^6$ and $R^7$ represents a cycloalkyl group represented by formula (5). Furthermore, both of $R^6$ and $R^7$ are preferably cycloalkyl group represented by formula (5) in terms of the ease of synthesis.

As the alkoxy group as being Y, $R^6$ and $R^7$, preferred are those having 1 to 20 carbon atoms including methoxy group, ethoxy group, propoxy group and isopropoxy group. As the aryloxy group as being Y, $R^6$ and $R^7$, preferred are those having 6 to 24 carbon atoms including phenoxy group. Examples of the silyl group as being Y, $R^6$ and $R^7$ include trimethylsilyl group, and examples of the amino group include amino group, methylamino group and dimethylamino group. $R^6$ and $R^7$ may be the same or different from each other. Also, $R^6$ and $R^7$ may bond to each other to form a ring structure. $R^6$ and/or $R^7$ may bond to Y to form a ring structure. Specific examples of the hydrocarbon group having 1 to 30 carbon atoms which may be substituted by one or more groups selected from a halogen atom, alkoxy group and aryloxy group in Y, $R^6$ and $R^7$ include methyl group, ethyl group, n-propyl group, isopropyl group, n-butyl group, isobutyl group, sec-butyl group, t-butyl group, n-pentyl group, neopentyl group, n-hexyl group, cyclopropyl group, cyclobutyl group, cyclopentyl group, cyclohexyl group, cycloheptyl group, cyclooctyl group, 1-adamantyl group, trifluoromethyl group, benzyl group, 2'-methoxybenzyl group, 3'-methoxybenzyl group, 4'-methoxybenzyl group, 4'-trifluoromethylbenzyl group, phenyl group, 2-methylphenyl group, 3-methylphenyl group, 4-methylphenyl group, 2,6-dimethylphenyl group, 3,5-dimethylphenyl group, 2,4,6-trimethylphenyl group, 2-isopropylphenyl group, 3-isopropylphenyl group, 4-isopropylphenyl group, 2,6-diisopropylphenyl group, 3,5-diisopropylphenyl group, 2,4,6-triisopropylphenyl group, 2-t-cbutylphenyl group, 2-cyclohexylphenyl group, 2-methoxyphenyl group, 3-methoxyphenyl group, 4-methoxyphenyl group, 2,6-dimethoxyphenyl group, 3,5-dimethoxyphenyl group, 2,4,6-trimethoxyphenyl group, 4-fluorophenyl group, pentafluorophenyl group, 4-trifluoromethylphenyl group, 3,5-bis(trifluoromethyl)phenyl group, 1-naphthyl group, 2-naphthyl group, 2-furyl group, 2-biphenyl group, 2',6'-dimethoxy-2-biphenyl group, 2'-methyl-2-biphenyl group, 2',4',6'-triisopropyl-2-biphenyl group.

In formula (5), R represents an alkylene group having 1 to 14 carbon atoms which may have a substituent. $R^9$, $R^{10}$ and $R^{11}$ independently represent a hydrogen atom, alkoxy group, aryloxy group, silyl group, amino group or a hydrocarbon group having 1 to 30 carbon atoms which may be substituted by one or more group selected a halogen atom, alkoxy group or aryloxy group; and at least one of $R^9$ and $R^{10}$ is not a hydrogen atom. It is presumed that the substituent $R^9$ or $R^{10}$, which is not a hydrogen atom, inhibits the chain transfer of the polymer due to β-hydrogen elimination during the polymerization reaction and thereby improves the molecular weight of the obtained polymer. Specific examples of the alkoxy group, aryloxy group, silyl group, amino group or a hydrocarbon group having 1 to 30 carbon atoms which may be substituted by one or more group selected a halogen atom, alkoxy group or aryloxy group represented by $R^9$, $R^{10}$ and $R^{11}$ include the same as those mentioned as Y, $R^6$ and $R^7$. $R^9$, $R^{10}$ and $R^{11}$ may be the same or different from each other. $R^9$, $R^{10}$, $R^{11}$ and the above-mentioned alkylene group R may bond to each other to form a ring structure. The number of carbon atoms of alkylene group R is preferably 2 to 6, and more preferably 4.

At least one of $R^9$ and $R^{10}$ is preferably an alkyl group having 1 to 6 carbon atoms or a cycloalkyl group having 3 to 8 carbon atoms. Furthermore, it is preferable that at least one of $R^9$ and $R^{10}$ is an isopropyl group.

Specific examples of X—$R^6$ or X—$R^7$ moiety in the case where $R^6$ or $R^7$ is represented by formula (5) are given below. Here, Me represents a methyl group and the bond between X and M or that between X and Y is not shown.

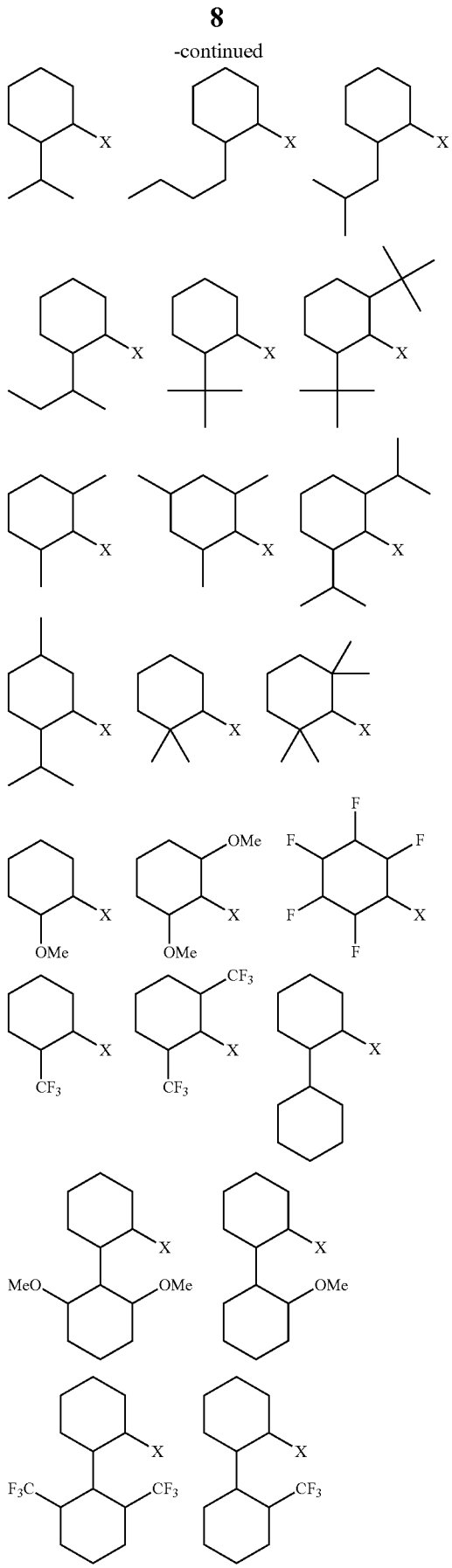

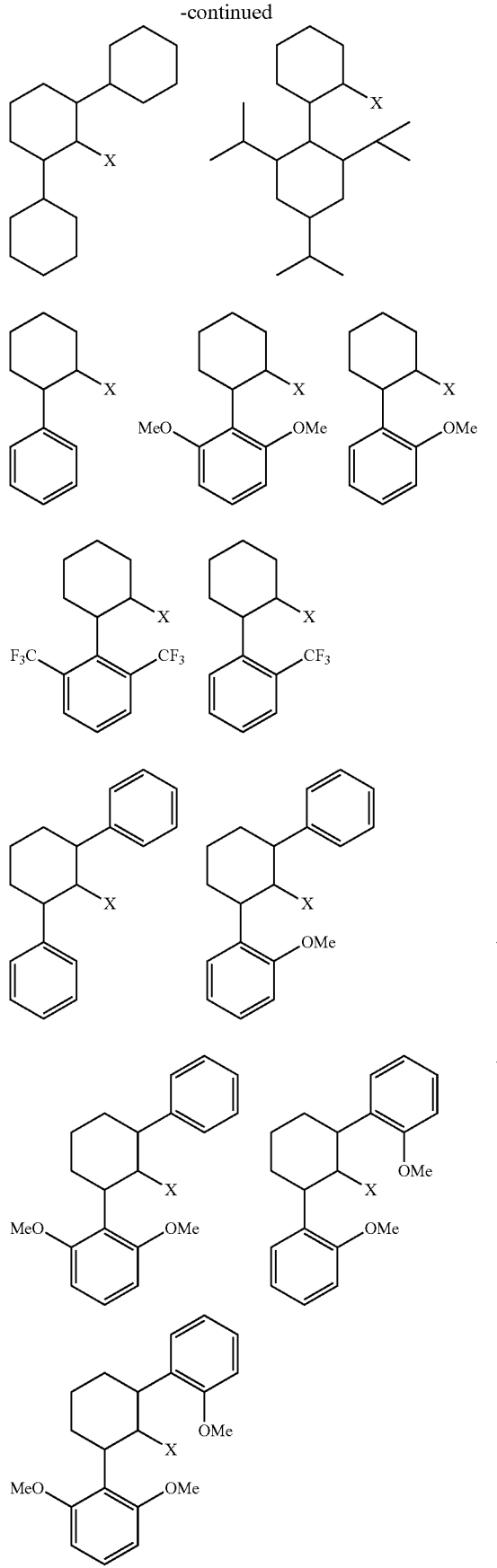
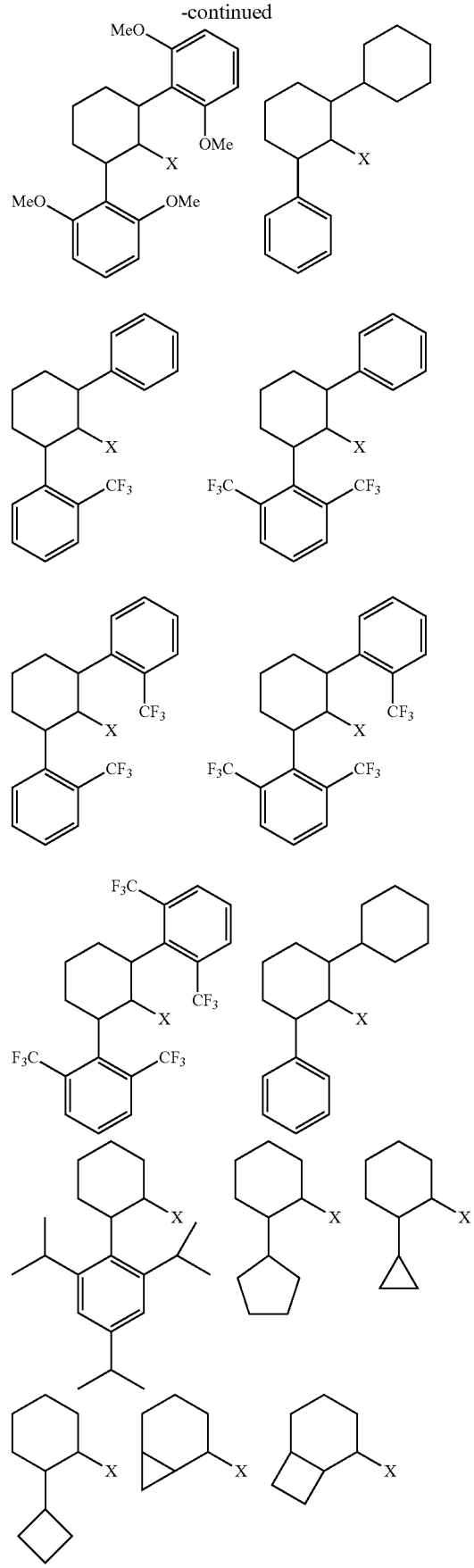

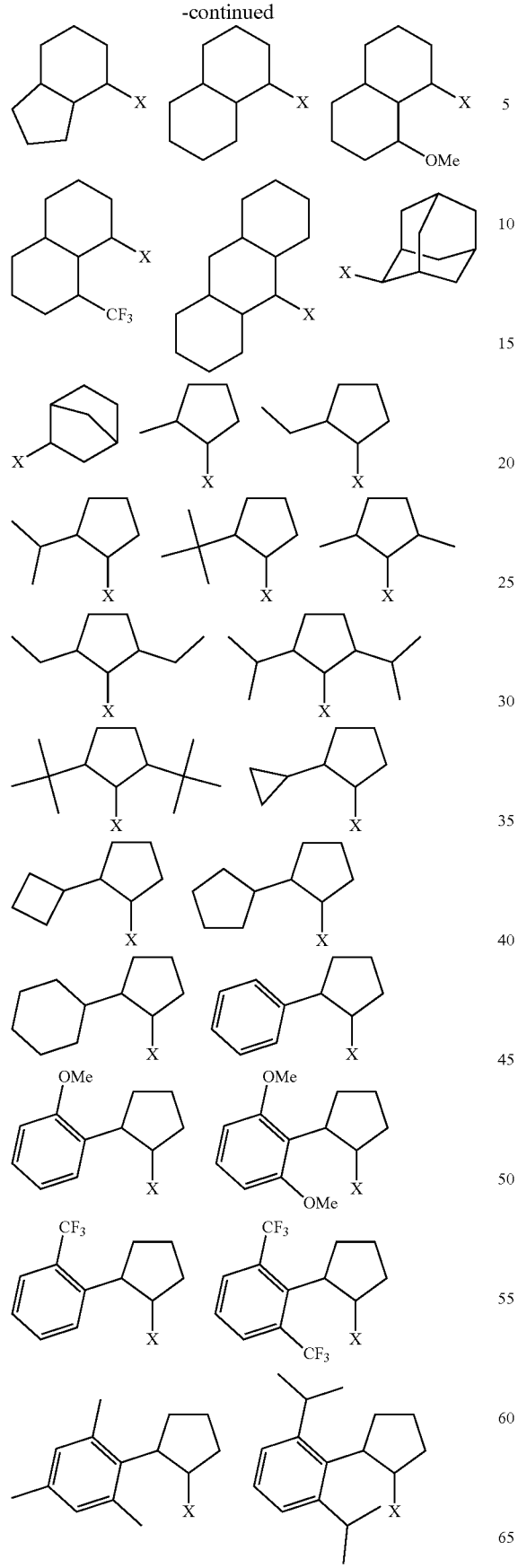
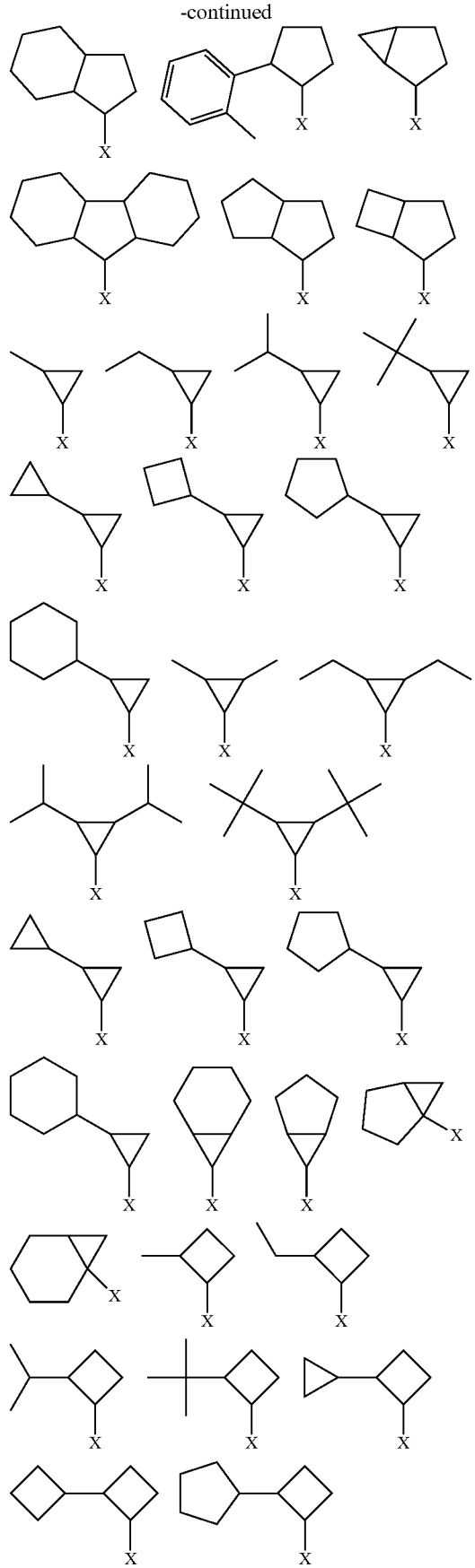

-continued

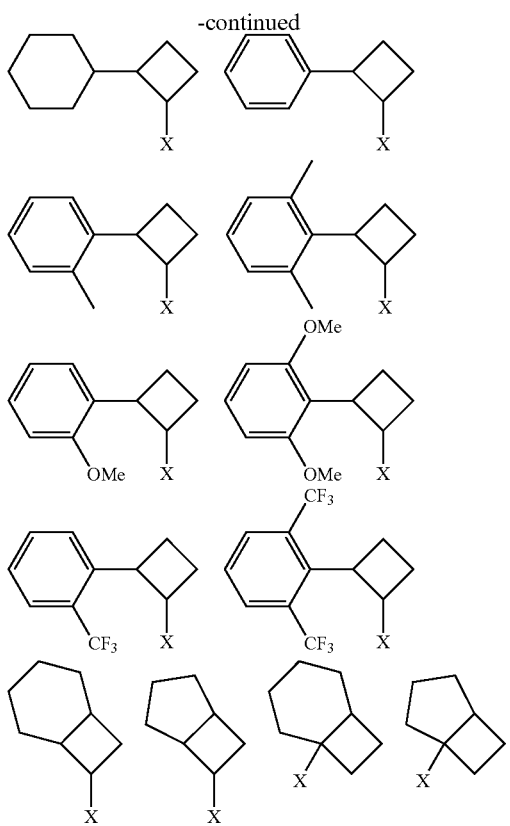

Among these, $R^6$ and $R^7$ are preferably a menthyl group represented by the following formula.

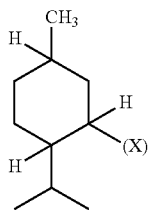

Furthermore, it is more preferable that both of $R^6$ and $R^7$ are a menthyl group.

Q represents a bivalent group indicated by —S(=O)$_2$—O—, —C(=O)—O—, —P(=O)(—OH)—O— or —S—, which is a moiety, wherein one electron coordinates to M. The left side of each of the above-mentioned formulae bonds to Z while the right side bonds to M. Among these, —S(=O)$_2$—O— is particularly preferable from the viewpoint of the catalyst activity.

Z represents a hydrogen atom or a hydrocarbon group having 1 to 40 carbon atoms which may be substituted by one or more groups selected from a halogen atom, alkoxy group and aryloxy group. Y and Z may bond to each other to form a ring structure. Specific examples of the halogen atom, alkoxy group and aryloxy group in the "hydrocarbon atom having 1 to 40 carbon atoms which may be substituted by one or more groups selected from a halogen atom, alkoxy group and aryloxy group" include those mentioned as the examples in Y, $R^6$ and $R^7$. Examples of hydrocarbon atom having 1 to 40 carbon atoms include methyl group, ethyl group, n-propyl group, isopropyl group, n-butyl group, t-butyl group, isobutyl group, sec-butyl group, cyclohexyl group, cyclopentyl group, phenyl group, 2-isopropylphenyl group, and 2,6-diisopropylphenyl group.

A single electron of an oxygen atom or a sulfur atom having high electronegativity of Z-Q moiety coordinates to metal atom M. Since the bonding electron between Z-Q-M is transferred from M to Z-Q, Z-Q and M may be indicated formally as an anion state and a cation state, respectively.

In formula (C1), Y moiety and Z moiety may bond to each other. In this case, formula (C1) can be represented by formula (C2). In formula (C2), Y—Z moiety as a whole is indicated by $Y^1$. Here, $Y^1$ represents a cross-linked structure between Q and X.

(C2)

In the formula, $Y^1$ represents a bivalent hydrocarbon group having 1 to 70 carbon atoms which may be substituted by one or more groups selected from a halogen atom, alkoxy group and aryloxy group. Q, M, X, $R^5$, $R^6$, $R^7$, L and q have the same meanings as in formula (C1).

Specific examples of a halogen atom, alkoxy group and aryloxy group as $Y^1$ are the same as those as Y. Examples of the hydrocarbon group having 1 to 70 carbon atoms include alkylene group and arylene group. Particularly preferred is arylene group.

Specific examples of $R^6$ and $R^7$ include those mentioned above.

The cross-linked structure $Y^1$ is the crosslinking moiety which binds X and Q moiety. Specific examples of the cross-linked structure $Y^1$ in which X is represented by a P atom are shown below. Here, multiple $R^9$s may be the same or different to each other and represent a hydrogen atom, halogen atom, hydrocarbon group having 1 to 20 carbon atoms, or a hydrocarbon group having 1 to 20 carbon atoms substituted by a halogen atom.

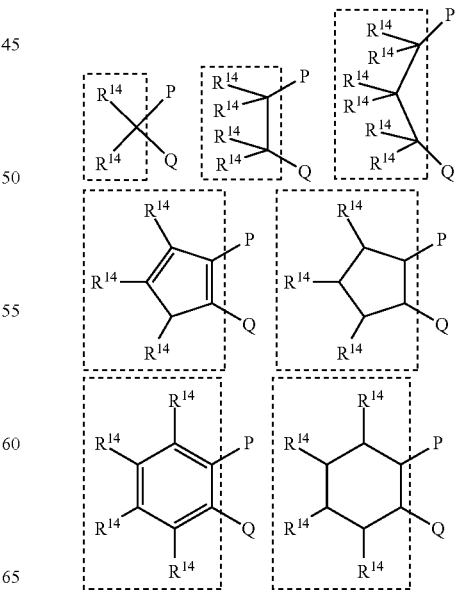

Substituents $R^6$ and $R^7$ may bond to $Y^1$ moiety to form a ring structure. Specific examples include the structures as follows. The examples described below show the case where substituent $R^6$ bonds to $Y^1$ moiety to form a ring structure.

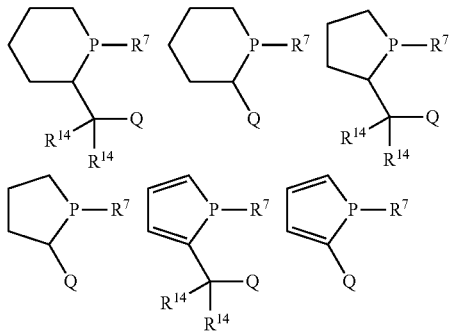

Among the catalysts represented by formula (C2), those represented by the following formula (C3) are particularly preferable.

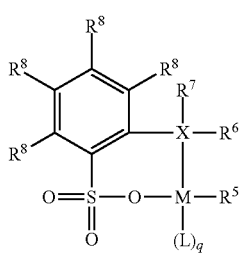

(C3)

In the formula, four $R^8$s independently represent a hydrogen atom, alkyl group having 1 to 8 carbon atoms, alkoxy group having 1 to 8 carbon atoms, aryloxy group having 6 to 18 carbon atoms or halogen atom; and M, $R^5$, $R^6$, $R^7$, L and q have the same meanings as those in formula (C1).

In formula (C3), preferred $R^5$ is an alkyl group having 1 to 6 carbon atoms, particularly methyl group. At least one of $R^6$ and $R^7$ is preferably a 2-isopropyl-5-methylcyclohexyl group (menthyl group), and particularly preferably, both of $R^6$ and $R^7$ are a menthyl group. M is preferably Pd.

Among the catalysts represented by formula (C3), those represented by the following formula (C4) are particularly preferable.

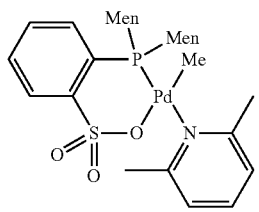

(C4)

The metal complex of the catalysts represented by formulae (C1) and (C2) can be synthesized according to the method similar to those described in known documents (for example, J. Am. Chem. Soc. 2007, 129, 8948). That is, a metal complex is synthesized by reacting zerovalent or bivalent M source with a ligand in formula (C1) or (C2).

The compound represented by formulae (C3) and (C4) can be synthesized by making $Y^1$ and Q in formula (C2) a specific group corresponding to formulae (C3) and (C4).

Examples of zerovalent M source include tris(dibenzylideneacetone) dipalladium as a palladium source and tetracarbonyl nickel(0) (Ni(CO)$_4$) and bis(1,5-cyclooctadiene)nickel as a nickel source.

Examples of bivalent M source include (1,5-cyclooctadiene) (methyl)palladium chloride, palladium chloride, palladium acetate, bis(acetonitrile)dichloropalladium (PdCl$_2$(CH$_3$CN)$_2$), bis(benzonitrile)dichloropalladium (PdCl$_2$(PhCN)$_2$), (N,N,N',N'-tetramethylethylenediamine)dichloro palladium(II) (PdCl$_2$(TMEDA)), (N,N,N',N'-tetramethylethylenediamine)dimethyl palladium (II) (PdMe$_2$(TMEDA)), palladium(II) acetylacetonate (Pd(acac)$_2$), (acac means "acetylacetonato"), palladium(II) trifluoromethanesulfonate (Pd(OSO$_2$CF$_3$)$_2$) as a palladium source and (allyl)nickel chloride, (allyl)nickel bromide, nickel chloride, nickel acetate, nickel(II) acetylacetonate (Ni (acac)$_2$), (1,2-dimethoxyethane)dichloronickel(II) (NiCl$_2$(DME)) and nickel(II) trifluoromethanesulfonate (Ni (OSO$_2$CF$_3$)$_2$) as a nickel source.

While an isolated metal complex represented by formula (C1) or (C2) can be used, the metal complex generated by bringing a M-containing metal source and a ligand precursor in the reaction system can also be used for in-situ polymerization without isolating the metal complex. Particularly, when $R^5$ in formulae (C1) and (C2) is a hydrogen atom, it is preferable to use the metal complex generated in situ after reacting a metal source containing zerovalent M and a ligand precursor for polymerization without isolating the metal complex.

In this case, a ligand precursors represented by formulae (C1-1) and (C1-2) can be used for a metal complex represented by formula (C1).

(Symbols in the formula have the same meanings as mentioned above.)

(Symbols in the formula have the same meanings as mentioned above.)

A ligand precursor represented by the following formula (C2-1) can be used for a metal complex represented by formula (C2).

(C2-1)

(Symbols in the formula have the same meanings as mentioned above.)

In formula (C1), it is preferable to select the ratio between the M source (M) and a ligand precursor (C1-1) (X) or a ligand precursor (C1-2) (Z) (i.e. X/M or Z/M) or the ratio between the M source (M) and a ligand precursor (C2-1) (C2 ligand) (i.e. (C2 ligand)/M) within the range of from 0.5 to 2.0, more preferably from 1.0 to 1.5.

When isolating the metal complex of formula (C1) or (C2), the one stabilized by making an electron-donating ligand (L) coordinate to the metal complex in advance may be used. In this case, q is ½, 1 or 2. q of ½ means that a bivalent electron-donating ligand coordinates to two metal complexes. q is preferably ½ or 1 to stabilize a metal complex catalyst. q of 0 means that there is no ligand in the precursor.

An electron-donating ligand (L) is a compound which contains an electron-donating group and is capable of stabilizing a metal complex by coordinating to metal atom M.

As the electron-donating ligand (L), examples of those containing a sulfur atom include dimethyl sulfoxide (DMSO). Examples of those containing a nitrogen atom include trialkylamine having 1 to 10 carbon atoms in alkyl group, dialkylamine having 1 to 10 carbon atoms in alkyl group, pyridine, 2,6-dimethylpyridine (otherwise known as "2,6-lutidine"), aniline, 2,6-dimethylaniline, 2,6-diisopropylaniline, N,N,N',N'-tetramethylethylenediamine (TMEDA), 4-(N,N-dimethylamino)pyridine (DMAP), acetonitrile, benzonitrile, quinoline and 2-methylquinoline. Examples of those containing an oxygen atom include diethyl ether, tetrahydrofuran and 1,2-dimethoxyethane. From the viewpoint of stability and catalytic activity of the metal complex, L is preferably dimethyl sulfoxide (DMSO), pyridine, 2,6-dimethylpyridine (otherwise known as "2,6-lutidine") and N,N,N',N'-tetramethylethylenediamine (TMEDA), and more preferably, dimethyl sulfoxide (DMSO), pyridine and 2,6-dimethylpyridine (otherwise known as "2,6-lutidine").

The metal complex represented by formula (C1), (C2) or (C3) may be supported on a support to be used for polymerization. In this case, there are no particular limitations on the support and examples include an inorganic support such as silica gel and alumina and an organic support such as polystyrene, polyethylene and polypropylene. Examples of the method for depositing a metal complex on a support include a physical adsorption method of impregnating the support with a solution of the metal complex and drying it and a method of depositing the metal complex onto a support by chemically bonding the metal complex to a support.

[Monomer]

Olefin, which is a first monomer used in the method for producing the polymer of the present invention, is represented by formula (1).

$$CH_2=CHR^1 \quad (1)$$

In formula (1), $R^1$ represents a hydrogen atom or hydrocarbon group having 1 to 20 carbon atoms. $R^1$ is preferably a hydrogen atom, alkyl group having 1 to 3 carbon atoms or aryl group having 6 to 20 carbon atoms. Specifically, examples of olefin represented by formula (1) include ethylene, propylene, 1-butene, 1-hexene, 4-methyl-1-pentene, 1-octene and styrene. Among these, ethylene is more preferable. One of these compounds may be used independently or two or more of them may be used in combination for polymerization.

Furthermore, a polar group-containing olefin and other monomers can be copolymerized in the present invention. A polar group-containing olefin, which is a second monomer used in the copolymerization in the present invention, is represented by formula (2).

$$CH_2=CR^2R^3 \quad (2)$$

In formula (2), $R^2$ represents a hydrogen atom or methyl group. $R^3$ represents —COOR$^{12}$, —CN, —OCOR$^{12}$, —OR$^{12}$, —CH$_2$—OCOR$^{12}$, —CH$_2$—OH, —CH$_2$—N(R$^{13}$)$_2$ or —CH$_2$-Hal (R$^{12}$ represents a hydrogen atom or hydrocarbon group having 1 to 5 carbon atoms, R$^{13}$ represents a hydrogen atom, hydrocarbon group having 1 to 5 carbon atoms, aromatic substituent having 6 to 18 carbon atoms or alkoxycarbonyl group; and Hal represents a halogen atom). $R^{12}$ is preferably a hydrogen atom or alkyl group having 1 to 3 carbon atoms, and particularly preferably a methyl group. $R^{13}$ is preferably a hydrogen atom, alkyl group having 1 to 3 carbon atoms, phenyl group, benzyl group, t-butoxycarbonyl group or benzyloxycarbonyl group. As a halogen atom, preferred are a chlorine atom and a bromine atom.

Specific examples of the polar group-containing olefin compound represented by formula (2) include vinyl acetate, allyl acetate, allyl alcohol, methyl methacrylate, methacrylic acid, methyl acrylate, acrylic acid, acrylonitrile, methyl vinyl ether, ethyl vinyl ether, allylamine, N-allylaniline, N-t-butoxycarbonyl-N-allylamine, N-benzyloxycarbonyl-N-allylamine, N-benzyl-N-allylamine, allyl chloride and allyl bromide. Among these, vinyl acetate, allyl acetate, methyl acetate and acrylonitrile are preferable. One of these compounds may be used independently or two or more of them may be used in combination.

Polar group-containing olefin represented by formula (2) is used in copolymerization with olefin represented by formula (1).

Examples of olefin represented by formula (1) and a polar group-containing olefin represented by formula (2) include ethylene and vinyl acetate, ethylene and allyl acetate, ethylene and allyl alcohol, ethylene and methyl methacrylate, ethylene and methacrylic acid, ethylene and methyl acrylate, ethylene and acrylic acid, ethylene and acrylonitrile, ethylene and methyl vinyl ether, ethylene and ethyl vinyl ether, ethylene and propyl vinyl ether, ethylene and allylamine, ethylene and N-allylaniline, ethylene and N-t-butoxycarbonyl-N-allylamine, ethylene and N-benzyloxycarbonyl-N-allylamine, ethylene and N-benzyl-N-allylamine, ethylene and allyl chloride, ethylene and allyl bromide, propylene and vinyl acetate, propylene and allyl acetate, propylene and allyl alcohol, propylene and methyl methacrylate, propylene and methacrylic acid, propylene and methyl acrylate, propylene and acrylic acid, propylene and acrylonitrile, propylene and methyl vinyl ether, propylene and ethyl vinyl ether, propylene and propyl vinyl ether, propylene and allylamine, propylene and N-allylaniline, propylene and N-t-butoxycarbonyl-N-allylamine, propylene and N-benzyloxycarbonyl-N-allylamine, propylene and N-benzyl-N-allylamine, propylene and allyl chloride, and propylene and allyl bromide. Among these, the combinations of ethylene and vinyl acetate, ethylene and allyl acetate, ethylene and allyl alcohol, ethylene and methyl methacrylate, ethylene and methyl acrylate, ethylene and acrylonitrile, ethylene and allyl chloride, and ethylene and allylamine are particularly preferable from the viewpoint of the polymer performance and economic efficiency.

In the method for producing a (co)polymer of the present invention, in addition to the monomers represented by formulae (1) and (2), one or more types of third monomer may be copolymerized. Examples of the third monomer include norbornene and carbon monoxide.

[Polymerization Method]

When the metal complex of the present invention is used as a catalyst, there are no particular limitations on the method of polymerizing monomers represented formulae (1) and (2) and the monomers can be polymerized by a widely-used method. That is, a process such as a solution polymerization method, a suspension polymerization method and a gas-phase polymerization method are available. Particularly preferred are a solution polymerization method and a suspension polymerization method. The polymerization style can be either of batch polymerization or continuous polymerization. Also, the polymerization can be conducted either by single-stage polymerization or multistage polymerization.

A mixture of two or more of the metal complex catalysts represented by formula (C1), (C2) or (C3) may be used for the polymerization reaction. Using the catalysts in mixture enables controlling the molecular weight and molecular weight distribution of the polymer and the content of the monomer unit derived from the monomer represented by formula (2) to thereby obtain a polymer suitable for the desired use.

The molar ratio between the metal complex catalyst represented by formula (C1), (C2) or (C3) and the total amount of monomers (monomers/metal complex) is within the range of from 1 to 10,000,000, preferably the range of from 10 to 1,000,000, more preferably the range of from 100 to 100,000.

There are no particular limitations on the polymerization temperature. The polymerization is generally conducted at a temperature in the range of from −30 to 400° C., preferably in the range of from 0 to 180° C., more preferably in the range of from 20 to 150° C.

The polymerization is conducted at a polymerization pressure, wherein the internal pressure consists mostly of the pressure of olefin represented by formula (1), in the range from normal pressure to 100 MPa, preferably in the range from normal pressure to 20 MPa and more preferably in the range from normal pressure to 10 MPa.

The polymerization time can be appropriately adjusted depending on the processing mode and the polymerization activity of the catalyst, and can be as short as several minutes or as long as several thousand hours.

It is preferable to fill the atmosphere in the polymerization system with an inert gas such as nitrogen and argon to prevent components other than monomers such as air, oxygen and moisture being mixed into the atmosphere to retain the catalyst activity. In the case of the solution polymerization, an inert solvent may be used in addition to monomers. There are no particular limitations on the inert solvent, and examples include aliphatic hydrocarbon such as isobutane, pentane, hexane, heptane and cyclohexane; aromatic hydrocarbon such as benzene, toluene and xylene; halogenated aliphatic hydrocarbon such as chloroform, methylene chloride, carbon tetrachloride, dichloroethane and tetrachloroethane; halogenated aromatic hydrocarbon such as chlorobenzene, dichlorobenzene and trichlorobenzene; aliphatic ester such as methyl acetate and ethyl acetate; and aromatic ester such as methyl benzoate and ethyl benzoate.

EXAMPLES

Hereinafter, the present invention is described in greater detail by referring to Examples and Comparative Examples. The present invention is by no means limited thereto.

[Method for Analyzing the Polymer Structure]

The structure of the (co)polymers obtained in Examples was determined by various analysis of the NMR spectra using JNM-ECS400 manufactured by JEOL Ltd. The content of the monomer unit derived from the polar group-containing olefin represented by formula (2) and the terminal structure of the copolymer was determined by analyzing $^{13}$C-NMR spectrum (90° pulse at 9.0 microseconds, spectrum width: 31 kHz, relaxation time: 10 seconds, acquisition time: 10 seconds, times of accumulating FID signals: 5,000 to 10,000 times) through the inverse-gated decoupling method at 120° C. using 1,2,4-trichlorobenzene (0.55 ml) as a solvent and Cr(acac)$_3$ (10 mg) as relaxation agent; or by analyzing $^1$H-NMR spectrum at 120° C. using 1,1,2,2-tetrachloroethane-d2 as a solvent.

A number average molecular weight and a weight average molecular weight were calculated by size extrusion chromatography in which polystyrene is employed as an internal standard substance using a high-temperature GPC apparatus, HLC-8121GPC/HT, manufactured by Tosoh Corporation, provided with TSKgel GMHHR-H(S) HT column (two columns of 7.8 mm I.D.×30 cm arranged in series) manufactured by Tosoh Corporation (solvent: 1,2-dichlorobenzene, temperature: 145° C.).

[Synthesis of Metal Complex Catalyst 1]

Metal complex catalyst 1 was synthesized according to the following reaction scheme:

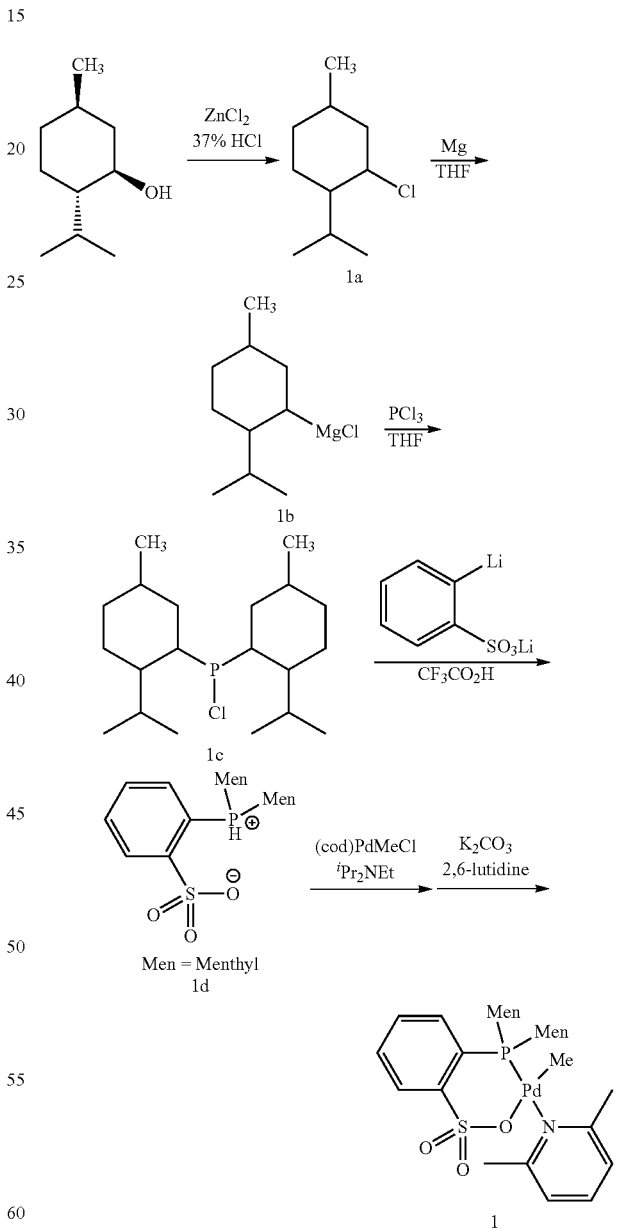

(a) Synthesis of Menthyl Chloride (Compound 1a)

Menthyl chloride (Compound 1a) was synthesized according to the method described in a literature (J. Org. Chem., 17, 1116. (1952)). That is, (−)-menthol (27 g, 0.17 mol) was added to the 37% hydrochloric acid solution (52 ml, 0.63 mol) of zinc chloride (77 g, 0.56 mol); the mixture was heated to 35° C. and stirred for five hours. After the reaction solution was cooled to room temperature, hexane (50 ml) was added thereto and an organic layer and an aqueous layer were separated using a separating funnel. After washing the organic layer with water (30 ml, one time), the layer was further washed with a concentrated sulfuric acid (10 ml, five times) and water (30 ml, five times). After drying the organic layer over magnesium sulfate, the layer was condensed under reduced pressure to obtain menthyl chloride (Complex 1a) as a colorless oily substance. The yield was 27 g (yield: 91%).

(b) Synthesis of Chlorodimenthylphosphine (Compound 1c)

Chlorodimenthylphosphine was synthesized according to the method described in a literature (Journal fur Praktische Chemie, 322, 485. (1980)). That is, a solution of menthylmagnesium chloride (Compound 1b) obtained by reacting menthyl chloride (Compound 1a; 2.6 g, 15 mmol) with magnesium (0.63 g, 26 mmol) in tetrahydrofuran (THF) (30 ml) on heating at 70° C. was added to a THF solution of phosphorous trichloride (0.63 ml, 7.2 mmol) at −78° C. After warming the solution to room temperature, the solution was heated to 70° C. and stirred for two hours. After the solvent was distilled away under reduced pressure, the solution was purified by distillation to obtain chlorodimenthylphosphine (Compound 1c). The yield was 0.62 g (yield: 25%).

$^{31}$P-NMR (162 MHz, THF): δ 123.9; separated solution (c) Synthesis of 2-(Dimenthylphosphino)Benzenesulfonic Acid (Compound 1d)

n-Butyllithium (1.6 M hexane solution, 1.4 ml, 2.3 mmol) was added to a THF solution (10 ml) of benzene sulfonic acid (0.18 g, 1.2 mmol) at 0° C. and stirred for one hour at room temperature. After cooling the reaction container to −78° C., chlorodimenthylphosphine (Compound 1c; 0.36 g, 1.1 mmol) was added thereto at −78° C. and stirred at room temperature for 15 hours. After terminating the reaction with trifluoroacetic acid (0.97 ml, 1.3 mmol), the solvent was distilled away under reduced pressure. The residue was dissolved in dichloromethane and washed with a saturated aqueous solution of ammonium chloride. After drying the organic layer over sodium sulfate, the solvent was distilled away under reduced pressure to obtain 2-(dimenthylphosphino)benzenesulfonic acid (Compound 1d) as a white powder. The yield was 0.31 g (yield: 63%).

$^1$H-NMR (500 MHz, CDCl$_3$): δ8.27 (br s, 1H), 7.77 (t, J=7.3 Hz, 1H), 7.59-7.52 (m, 2H), 3.54 (br s, 1H), 2.76 (br s, 1H), 2.16 (br s, 1H), 1.86-1.38 (m, 12H), 1.22-0.84 (m, 22H), 0.27 (br s, 1H);

$^{31}$P{$^1$H}-NMR (162 MHz, CDCl$_3$): δ 45.1 (br.), −4.2 (br.).

(d) Synthesis of Metal Complex Catalyst 1

(cod)PdMeCl (synthesized according to a literature; Inorg. Chem., 1993, 32, 5769-5778; cod=1,5-cyclooctadiene, 0.079 g, 0.30 mmol) was added to a methylene chloride solution (10 ml) of 2-(dimenthylphospino)benzenesulfonic acid (Compound 1d; 0.14 g, 0.30 mmol) and N,N-diisopropylethylamine (0.26 ml, 1.5 mmol) and the solution was stirred for one hour at room temperature. After condensing the solution, the residue was dissolved in methylene chloride (10 ml), and the resultant solution was added to a methylene chloride suspension (2 ml) of potassium carbonate (0.42 g, 3.0 mmol) and 2,6-lutidine (0.35 ml, 3.0 mmol) and the resultant was stirred for one hour at room temperature. After filtering the reaction solution through by Celite (dry diatom earth) and Florisil (magnesium silicate), the solvent was condensed and dried under reduced pressure to obtain metal complex catalyst 1. The yield was 0.17 g (yield: 80%).

$^1$H-NMR (400 MHz, CDCl$_3$): δ 8.26 (ddd, J=7.8, 3.9, 1.4 Hz, 1H), 7.81 (t, J=7.9 Hz, 1H), 7.56 (t, J=7.7 Hz, 1H), 7.49 (t, J=7.6 Hz, 1H), 7.43 (t, J=7.4 Hz, 1H), 7.13 (d, J=7.8 Hz, 1H), 7.08 (d, J=7.6 Hz, 1H), 3.75 (s, 1H), 3.24 (s, 3H), 3.17 (s, 3H), 2.59 (s, 1H), 2.49-2.39 (m, 2H), 2.29-2.27 (m, 1H), 2.05-1.96 (m, 1H), 1.89-1.37 (m, 12H), 1.21-1.11 (m, 2H), 0.98 (d, J=6.6 Hz, 3H), 0.95 (d, J=6.2 Hz, 3H), 0.84 (d, J=6.6 Hz, 3H), 0.78 (d, J=6.6 Hz, 3H), 0.58 (d, J=6.6 Hz, 3H), 0.41 (d, J=2.3 Hz, 3H), 0.08 (d, J=6.6 Hz, 3H);

$^{31}$P-NMR (162 MHz, CDCl$_3$): δ 16.6.

[Synthesis of Polymers]

Homopolymerization of olefin represented by formula (C1) and copolymerization of olefin represented by formula (C1) and the polar group-containing olefin represented by formula (C2) were conducted using metal complex catalyst 1 synthesized by the above-mentioned method. The polymerization conditions and polymerization results are shown in Tables 0.1 and 2, respectively.

Here, the catalyst concentration and the catalytic activity were calculated by the following formulae.

Catalyst concentration (mmol/l)=Molar number of the used metal complex catalyst (mmol)×1000/ (toluene volume (ml)+volume of the polar group-containing monomer (ml))

Catalytic activity (g/mmol·h)=Yield of the obtained copolymer (g)/(Molar number of the used metal complex catalyst (mmol)×reaction time (h))

Example 1

Copolymerization of Allyl Acetate and Ethylene (Preparation of Polymer 1)

Toluene (12 ml) and allyl acetate (3 ml, 28 mmol) were added to a 50 ml-volume autoclave containing metal complex catalyst 1 (34.6 mg, 0.050 mmol) under argon atmosphere. After filling the autoclave with ethylene (3.0 MPa), the content of the autoclave was stirred at 80° C. for 15 hours. After cooling the autoclave to room temperature, methanol (about 20 ml) was added thereto. The generated copolymer was collected by filtration, washed with methanol and dried under reduced pressure to obtain polymer 1. The yield was 2.0 g. The catalytic activity was calculated to be 2.7 g/(mmol·h). The number average molecular weight and weight average molecular weight of the copolymer were calculated 95,000 and 142,000, respectively, by size exclusion chromatography and Mw/Mn was 1.5. The allyl acetate content in the copolymer was determined to be 100:1.8 by molar ratio of ethylene to allyl acetate (molar fraction of allyl acetate=1.7%) by $^1$H-NMR spectrum.

Example 2

Copolymerization of Allyl Acetate and Ethylene (Preparation of Polymer 2)

The copolymerization of allyl acetate and ethylene was conducted in a similar manner as in Example 1 by changing the volume ratio of toluene and allyl acetate. That is, toluene (9 ml) and allyl acetate (6 ml, 56 mmol) were added to a 50 ml-volume autoclave containing metal complex catalyst 1 (34.6 mg, 0.050 mmol) under argon atmosphere. After filling the autoclave with ethylene (3.0 MPa), the content of the autoclave was stirred at 80° C. for 15 hours. After cooling the autoclave to room temperature, methanol (about 20 ml) was added thereto. The generated copolymer was collected by filtration, washed with methanol and dried under reduced pressure to obtain polymer 2. The yield was 1.9 g. The catalytic activity was calculated to be 2.5 g/(mmol·h). The number average molecular weight and weight average molecular weight of the copolymer were calculated 79,000 and 125,000, respectively, by size exclusion chromatography and Mw/Mn was 1.5. The allyl acetate content in the copolymer was determined to be 100:2.9 by molar ratio of ethylene to allyl acetate (molar fraction of allyl acetate=2.8%) by $^1$H-NMR spectrum.

Example 3

Copolymerization of Allyl Acetate and Ethylene (Preparation of Polymer 3)

The copolymerization of allyl acetate and ethylene was conducted in a similar manner in Examples 1 and 2 by changing the volume ratio of toluene and allyl acetate, reaction scale and catalyst concentration. That is, toluene (37.5 ml) and allyl acetate (37.5 ml, 350 mmol) were added to a 120 ml-volume autoclave containing metal complex catalyst 1 (6.9 mg, 0.010 mmol) under nitrogen atmosphere. After filling the autoclave with ethylene (3.0 MPa), the content of the autoclave was stirred at 80° C. for five hours. After cooling the autoclave to room temperature, the reaction solution in the autoclave was added to methanol (300 ml). The generated copolymer was collected by filtration, washed with methanol and dried under reduced pressure to obtain polymer 3. The yield was 0.63 g. The catalytic activity was calculated to be 13 g/(mmol·h). The number average molecular weight and weight average molecular weight of the copolymer were calculated 170,000 and 470,000, respectively, by size exclusion chromatography and Mw/Mn was 2.9. The allyl acetate content in the copolymer was determined to be 100:2.9 by molar ratio of ethylene to allyl acetate (molar fraction of allyl acetate=2.8%) by $^1$H-NMR spectrum.

Example 4

Copolymerization of Allyl Acetate and Ethylene (Preparation of Polymer 4)

The copolymerization of allyl acetate and ethylene was conducted in a similar manner in Example 3 by changing the volume ratio of toluene and allyl acetate, reaction scale and reaction time. That is, allyl acetate (300 ml, 2,800 mmol) was added to a 500 ml-volume autoclave containing metal complex catalyst 1 (13.9 mg, 0.020 mmol) under nitrogen atmosphere. After filling the autoclave with ethylene (4.0 MPa), the content of the autoclave was stirred at 80° C. for 43 hours. After cooling the autoclave to room temperature, the reaction solution in the autoclave was added to methanol (1 l). The generated copolymer was collected by filtration, washed with methanol and dried under reduced pressure to obtain polymer 4. The yield was 6.8 g. The catalytic activity was calculated to be 7.9 g/(mmol·h). The number average molecular weight and weight average molecular weight of the copolymer were calculated 290,000 and 790,000, respectively, by size exclusion chromatography and Mw/Mn was 2.7. The allyl acetate content in the copolymer was determined to be 100:2.7 by molar ratio of ethylene to allyl acetate (molar fraction of allyl acetate=2.6%) by $^1$H-NMR spectrum.

Comparative Example 1

Copolymerization of Allyl Acetate and Ethylene Using Metal Complex Catalyst 2 (Preparation of Comparative Polymer 1)

The copolymerization of allyl acetate and ethylene was conducted in a similar manner as in Example 1 by using metal complex catalyst 2 represented by the formula described below (synthesized according to a literature: J. Am. Chem. Soc., 2009, 131, 14606-14607) instead of metal complex catalyst 1.

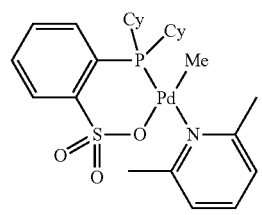

Cy = Cyclohexyl

That is, toluene (12 ml) and allyl acetate (3 ml, 28 mmol) were added to a 50 ml-volume autoclave containing metal complex catalyst 2 (58.2 g, 0.10 mmol) under argon atmosphere. After filling the autoclave with ethylene (3.0 MPa), the content of the autoclave was stirred at 80° C. for three hours. After cooling the autoclave to room temperature, methanol (about 20 ml) was added thereto. The generated copolymer was collected by filtration, washed with methanol and dried under reduced pressure to obtain a copolymer (comparative polymer 1). The yield was 1.7 g. The catalytic activity was calculated to be 5.7 g/(mmol·h). The number average molecular weight and weight average molecular weight of the copolymer were calculated 15,000 and 35,000, respectively, by size exclusion chromatography and Mw/Mn was 2.3. The allyl acetate content in the copolymer was determined to be 100:1.3 by molar ratio of ethylene to allyl acetate (molar fraction of allyl acetate=1.2%) by $^{13}$C-NMR spectrum.

Comparative Example 2

Copolymerization of Allyl Acetate and Ethylene (Preparation of Comparative Polymer 2)

The copolymerization of allyl acetate and ethylene was conducted in a similar manner as in Example 1 by metal complex catalyst 3 represented by the formula described below (synthesized according to a literature: J. Am. Chem. Soc., 2007, 129, 8948-8949) instead of metal complex catalyst 1.

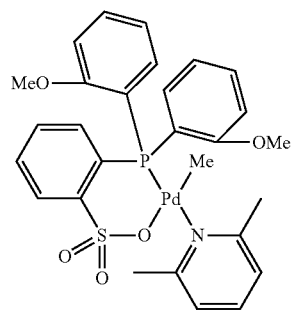

That is, methylene chloride (3.75 ml), toluene (3.75 ml) and allyl acetate (7.5 ml, 70 mmol) were added to a 50 ml-volume autoclave containing metal complex catalyst 3 (63.0 g, 0.10 mmol) under argon atmosphere. After filling the autoclave with ethylene (3.0 MPa), the content of the autoclave was stirred at 80° C. for three hours. After cooling the autoclave to room temperature, methanol (about 20 ml) was added thereto. The generated copolymer was collected by filtration, washed with methanol and dried under reduced pressure to obtain a copolymer (comparative polymer 2). The yield was 0.29 g. The catalytic activity was calculated to be 0.97 g/(mmol·h). The number average molecular weight and weight average molecular weight of the copolymer were calculated 4,000 and 7,000, respectively, by size exclusion chromatography and Mw/Mn was 1.7. The allyl acetate content in the copolymer was determined to be 100:3.8 by molar ratio of ethylene to allyl acetate (molar fraction of allyl acetate=3.7%) by $^{13}$C-NMR spectrum.

Comparative Example 3

Copolymerization of Allyl Acetate and Ethylene (Preparation of Comparative Polymer 3)

The copolymerization of allyl acetate and ethylene was conducted in a similar manner as in Example 3 by metal complex catalyst 4 represented by the formula described below (synthesized according to Patent Document 1: JP-A-2011-68881) instead of metal complex catalyst 1.

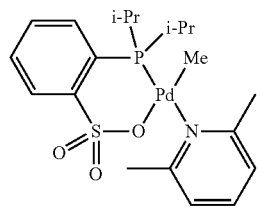

i-Pr = isopropyl

That is, toluene (37.5 ml) and allyl acetate (37.5 ml, 350 mmol) were added to a 120 ml-volume autoclave containing metal complex catalyst 4 (50.2 mg, 0.10 mmol) under nitrogen atmosphere. After filling the autoclave with ethylene (3.0 MPa), the content of the autoclave was stirred at 80° C. for five hours. After cooling the autoclave to room temperature, the reaction solution in the autoclave was added to methanol (about 100 ml). The generated copolymer was collected by filtration, washed with methanol and dried under reduced pressure to obtain a copolymer (comparative polymer 3). The yield was 3.0 g. The catalyst activity was calculated to be 6.0 g/(mmol·h). The number average molecular weight and weight average molecular weight of the copolymer were calculated 11,000 and 26,000, respectively, by size exclusion chromatography and Mw/Mn was 2.4. The allyl acetate content in the copolymer was determined to be 100:4.1 by molar ratio of ethylene to allyl acetate (molar fraction of allyl acetate=4.0%) by $^{13}$C-NMR spectrum.

Comparative Example 4

Copolymerization of Allyl Acetate and Ethylene Using Metal Complex Catalyst 5 (Preparation of Comparative Polymer 4)

The copolymerization of allyl acetate and ethylene was conducted in a similar manner as in Example 3 by metal complex catalyst 5 represented by the formula described below (synthesized according to Patent Document 1; JP-A-2011-68881) instead of metal complex catalyst 1.

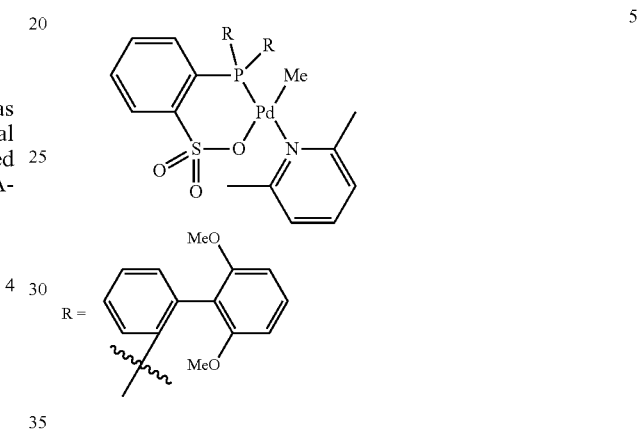

That is, toluene (37.5 ml) and allyl acetate (37.5 ml, 350 mmol) were added to a 120 ml-volume autoclave containing metal complex catalyst 5 (84.2 mg, 0.10 mmol) under nitrogen atmosphere. After filling the autoclave with ethylene (3.0 MPa), the content of the autoclave was stirred at 80° C. for five hours. After cooling the autoclave to room temperature, the reaction solution in the autoclave was added to methanol (about 100 ml). The generated copolymer was collected by filtration, washed with methanol and dried under reduced pressure to obtain a copolymer (comparative polymer 4). The yield was 0.21 g. The catalytic activity was calculated to be 0.42 g/(mmol·h). The number average molecular weight and weight average molecular weight of the copolymer were calculated 37,000 and 85,000, respectively, by size exclusion chromatography and Mw/Mn was 2.3. The allyl acetate content in the copolymer was determined to be 100:1.3 by molar ratio of ethylene to allyl acetate (molar fraction of allyl acetate=1.2%) by $^{13}$C-NMR spectrum.

TABLE 1

| Examples | Monomer of formula (1) Ethylene (MPa) | Monomer of formula (2) Allyl acetate (ml) | Metal complex catalyst (mmol) | Solvent (ml) | Catalyst concentration mmol/l | Reaction temperature (C.°) | Reaction time (hr) |
|---|---|---|---|---|---|---|---|
| Ex. 1 | 3.0 | 3 | 1 (0.050) | toluene (12) | 3.3 | 80 | 15 |
| Ex. 2 | 3.0 | 6 | 1 (0.050) | toluene (9) | 3.3 | 80 | 15 |
| Comparative Ex. 1 | 3.0 | 3 | 2 (0.10) | toluene (12) | 6.7 | 80 | 3 |
| Comparative Ex. 2 | 3.0 | 7.5 | 3 (0.10) | methylene chloride (3.75)/ toluene (3.75) | 6.7 | 80 | 3 |

TABLE 1-continued

| Examples | Monomer of formula (1) Ethylene (MPa) | Monomer of formula (2) Allyl acetate (ml) | Metal complex catalyst (mmol) | Solvent (ml) | Catalyst concentration mmol/l | Reaction temperature (C.°) | Reaction time (hr) |
| --- | --- | --- | --- | --- | --- | --- | --- |
| Ex. 3 | 3.0 | 37.5 | 1 (0.010) | toluene (37.5) | 0.13 | 80 | 5 |
| Comparative Ex. 3 | 3.0 | 37.5 | 4 (0.10) | toluene (37.5) | 1.3 | 80 | 5 |
| Comparative Ex. 4 | 3.0 | 37.5 | 5 (0.10) | toluene (37.5) | 1.3 | 80 | 5 |
| Ex. 4 | 4.0 | 300 | 1 (0.020) | None | 0.067 | 80 | 43 |

TABLE 2

| Examples | Polymer No. | Polymer yield (g) | Catalyst Activity (g/mmol·h) | Color of polymer | Molecular weight | | | Molar fraction of allyl acetate (mol %) |
| --- | --- | --- | --- | --- | --- | --- | --- | --- |
| | | | | | Mn | Mw | Mw/Mn | |
| Ex. 1 | 1 | 2.0 | 2.7 | white | 95,000 | 142,000 | 1.5 | 1.7 |
| Ex. 2 | 2 | 1.9 | 2.5 | white | 79,000 | 125,000 | 1.5 | 2.8 |
| Comparative Ex. 1 | Comparative 1 | 1.7 | 5.7 | white | 15,000 | 35,000 | 2.3 | 1.2 |
| Comparative Ex. 2 | Comparative 2 | 0.29 | 0.97 | gray | 4,000 | 7,000 | 1.7 | 3.7 |
| Ex. 3 | 3 | 0.63 | 13 | white | 170,000 | 470,000 | 2.9 | 2.8 |
| Comparative Ex. 3 | Comparative 3 | 3.0 | 6.0 | white | 11,000 | 26,000 | 2.4 | 4.0 |
| Comparative Ex. 4 | Comparative 4 | 0.21 | 0.42 | gray | 37,000 | 85,000 | 2.3 | 1.2 |
| Ex. 4 | 4 | 6.8 | 7.9 | white | 290,000 | 790,000 | 2.7 | 2.6 |

As in Tables 1 and 2, high molecular weight copolymers of allyl monomers were able to be synthesized in Examples 1 to 4 by using metal complex catalyst 1 of the present invention, which copolymers were difficult to be produced by using conventional catalysts (Comparative Examples 1 to 4). Also, the polymer obtained in Example 3 in which the metal complex catalyst was in a low concentration exhibited higher catalytic activity than in Examples 1 and 2.

Furthermore, homopolymerization of ethylene as being olefin represented by formula (1) and copolymerization of ethylene and olefin having a polar group represented by formula (2) excluding allyl acetate were conducted using metal complex catalyst 1. The polymerization conditions and polymerization results are shown in Tables 3 and 4, respectively.

Example 5

Homopolymerization of Ethylene (Preparation of Polymer 5)

Toluene (100 ml) was added to a 300 ml-volume autoclave containing metal complex catalyst 1 (6.9 mg, 0.010 mmol) under argon atmosphere. After filling the autoclave with ethylene (3.0 MPa), the content of the autoclave was stirred at 80° C. for one hour. After cooling the autoclave to room temperature, methanol (about 150 ml) was added thereto. The generated copolymer was collected by filtration, washed with methanol and dried under reduced pressure to obtain polymer 5. The yield was 2.1 g. The catalytic activity was calculated to be 205 g/(mmol·h). The number average molecular weight and weight average molecular weight of the copolymer were calculated 405,000 and 618,000, respectively, by size exclusion chromatography and Mw/Mn was 1.5.

Example 6

Copolymerization of Methyl Acrylate and Ethylene (Preparation of Polymer 6)

Toluene (7.5 ml) and methyl acrylate (7.5 ml, 84 mmol) were added to a 50 ml-volume autoclave containing metal complex catalyst 1 (6.9 mg, 0.010 mmol) under argon atmosphere. After filling the autoclave with ethylene (3.0 MPa), the content of the autoclave was stirred at 80° C. for three hours. After cooling the autoclave to room temperature, methanol (about 20 ml) was added thereto. The generated copolymer was collected by filtration, washed with methanol and dried under reduced pressure to obtain polymer 6. The yield was 2.0 g. The catalytic activity was calculated to be 67 g/(mmol·h). The number average molecular weight and weight average molecular weight of the copolymer were calculated 55,000 and 171,000, respectively, by size exclusion chromatography and Mw/Mn was 3.1. The allyl acetate content in the copolymer was determined to be 100:1.3 by molar ratio of ethylene to methyl acrylate (molar fraction of methyl acrylate=1.3%) by $^1$H-NMR spectrum.

Example 7

Copolymerization of Butyl Vinyl Ether and Ethylene (Preparation of Polymer 7)

A copolymer of butyl vinyl ether and ethylene (polymer 7) was produced in a similar manner as in Example 6 except for changing toluene and methyl acrylate to toluene (10 ml) and butyl vinyl ether (5 ml, 39 mmol), and reaction time to 15 hours. The results are shown in Tables 3 and 4.

Example 8

Copolymerization of Acrylonitrile and Ethylene (Preparation of Polymer 8)

A copolymer of acrylonitrile and ethylene (polymer 8) was produced in a similar manner as in Example 6 except for changing toluene and methyl acrylate to toluene (2.5 ml) and acrylonitrile (2.5 ml, 38 mmol), reaction temperature to 100° C., and reaction time to 96 hours. The results are shown in Tables 3 and 4.

Example 9

Copolymerization of Vinyl Acetate and Ethylene (Preparation of Polymer 9)

A copolymer of vinyl acetate and ethylene (polymer 9) was produced in a similar manner as in Example 6 except for changing toluene and methyl acrylate to toluene (3 ml) and vinyl acetate (12 ml, 130 mmol), reaction temperature to 80° C., and reaction time to 15 hours. The results are shown in Tables 3 and 4.

Comparative Example 5

Homopolymerization of Ethylene Using Metal Complex Catalyst 2 (Preparation of Comparative Polymer 5)

Homopolymerization of ethylene was conducted in a similar manner as in Example 5 using metal complex catalyst 2 instead of metal complex catalyst 1. That is, Toluene (75 ml) was added to a 120 ml-volume autoclave containing metal complex catalyst 2 (29 mg, 0.050 mmol) under nitrogen atmosphere. After filling the autoclave with ethylene (3.0 MPa), the content of the autoclave was stirred at 80° C. for one hour. After cooling the autoclave to room temperature, the reaction solution was added to methanol (300 ml). The generated polymer was collected by filtration, washed with methanol and dried under reduced pressure to obtain comparative polymer 5. The results are shown in Tables 3 and 4.

Comparative Example 6

Copolymerization of Methyl Acrylate and Ethylene Using Metal Complex Catalyst 4 (Preparation of Comparative Polymer 6)

Copolymerization of methyl acrylate and ethylene was conducted in a similar manner as in Example 6 using metal complex catalyst 4 instead of metal complex catalyst 1. That is, toluene (37.5 ml) and methyl acrylate (37.5 ml, 420 mmol) were added to a 120 ml-volume autoclave containing metal complex catalyst 4 (50 mg, 0.10 mmol) under nitrogen atmosphere. After filling the autoclave with ethylene (3.0 MPa), the content of the autoclave was stirred at 80° C. for three hours. After cooling the autoclave to room temperature, the reaction solution was added to methanol (about 300 ml). The generated polymer was collected by filtration, washed with methanol and dried under reduced pressure to obtain comparative polymer 6. The results are shown in Tables 3 and 4.

Comparative Example 7

Copolymerization of Acrylonitrile and Ethylene Using Metal Complex Catalyst 3 (Preparation of Comparative Polymer 7)

A literature (J. Am. Chem. Soc., 2007, 129, 8948-8949) describes copolymerization of acrylonitrile and ethylene using metal complex catalyst 3. That is, polymerization was conducted in an autoclave containing toluene (2.5 ml) and acrylonitrile (2.5 ml), filled with ethylene (3.0 MPa), using metal complex catalyst 3 (0.010 mmol) at 100° C. for 120 hours to obtain 0.23 g of comparative polymer 7. The results are shown in Tables 3 and 4.

Comparative Example 8

Copolymerization of Vinyl Acetate and Ethylene Using Metal Complex Catalyst 2 (Preparation of Comparative Polymer 8)

A literature (J. Am. Chem. Soc., 2009, 131, 14606-14607) describes copolymerization of vinyl acetate and ethylene using metal complex catalyst 2. That is, polymerization was conducted in an autoclave containing toluene (3 ml) and vinyl acetate (12 ml), filled with ethylene (3.0 MPa), using metal complex catalyst 2 (0.10 mmol) at 80° C. for 15 hours to obtain 1.0 g of comparative polymer 8. The results are shown in Tables 3 and 4.

TABLE 3

| Examples | Monomer of formula (1) Ethylene (MPa) | Monomer of formula (2) kinds (ml) | Metal complex catalyst (mmol) | Solvent (ml) | Reaction temperature (C.°) | Reaction time (hr) |
|---|---|---|---|---|---|---|
| Ex. 5 | 3.0 | None | 1 (0.010) | toluene (100) | 80 | 1 |
| Comparative Ex. 5 | 3.0 | None | 2 (0.050) | toluene (75) | 80 | 1 |
| Ex. 6 | 3.0 | methyl acrylate (7.5) | 1 (0.10) | toluene (7.5) | 80 | 3 |
| Comparative Ex. 6 | 3.0 | methyl acrylate (37.5) | 4 (0.10) | toluene (37.5) | 80 | 3 |
| Ex. 7 | 3.0 | butylvinyl ether (5) | 1 (0.010) | toluene (10) | 80 | 15 |
| Ex. 8 | 3.0 | acrylonitrile (2.5) | 1 (0.010) | toluene (2.5) | 100 | 96 |
| Comparative Ex. 7 | 3.0 | acrylonitrile (2.5) | 3 (0.10) | toluene (2.5) | 100 | 120 |
| Ex. 9 | 3.0 | vinyl acetate (12) | 1 (0.010) | toluene (3) | 80 | 15 |
| Comparative Ex. 8 | 3.0 | vinyl acetate (12) | 2 (0.10) | toluene (3) | 80 | 15 |

TABLE 4

| Polymer Examples | Polymer No. | Polymer yield (g) | Catalyst Activity (g/mmol · h) | Molecular weight Mn | Molecular weight Mw | Molecular weight Mw/Mn | Molar fraction of polar group-containing monomer units (mol %) |
|---|---|---|---|---|---|---|---|
| Ex. 5 | 5 | 2.1 | 205 | 405,000 | 618,000 | 1.5 | — |
| Comparative Ex. 5 | Comparative 5 | 8.3 | 166 | 30,000 | 69,000 | 2.3 | — |
| Ex. 6 | 6 | 2.0 | 67 | 55,000 | 171,000 | 3.1 | 1.3 |
| Comparative Ex. 6 | Comparative 6 | 6.7 | 22 | 7,500 | 15,000 | 2.0 | 10.9 |
| Ex. 7 | 7 | 3.9 | 26 | 55,000 | 151,000 | 2.8 | 1.4 |
| Ex. 8 | 8 | 0.84 | 0.87 | 24,000 | 56,000 | 2.3 | 1.5 |
| Comparative Ex. 7 | Comparative 7 | 0.23 | 0.19 | 2,900 | 4,400 | 1.5 | 9.0 |
| Ex. 9 | 9 | 0.34 | 2.3 | 13,000 | 33,000 | 2.5 | 1.3 |
| Comparative Ex. 8 | Comparative 8 | 1.0 | 0.67 | 5,800 | 13,000 | 2.3 | 1.9 |

As in Tables 3 and 4, high molecular weight copolymers of polyethylene and polar group-containing monomers were able to be synthesized by using metal complex catalyst 1 of the present invention, which copolymers were difficult to be produced by using conventional catalysts of metal complex of group 10 elements in the periodic system (Comparative Examples 5 to 8).

The invention claimed is:

1. A method for producing a homopolymer or copolymer of monomers comprising olefin represented by formula (1)

$$CH_2=CHR^1 \quad (1)$$

in the formula, $R^1$ represents a hydrogen atom or hydrocarbon group having 1 to 20 carbon atoms, using as a polymerization catalyst a metal complex represented by formula (C1)

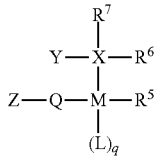
(C1)

in the formula, M represents a metal atom of group 10 element in the periodic system; X represents a phosphorous atom (P) or an arsenic atom (As); $R^5$ represents a hydrogen atom or hydrocarbon group having 1 to 30 carbon atoms which is optionally substituted by one or more groups selected from a halogen atom, alkoxy group, aryloxy group and acyloxy group; Y, $R^6$ and $R^7$ independently represent a hydrogen atom, alkoxy group, aryloxy group, silyl group, amino group or hydrocarbon group having 1 to 30 carbon atoms which is optionally substituted by one or more groups selected from a halogen atom, alkoxy group and aryloxy group; and at least one of $R^6$ and $R^7$ represents a cycloalkyl group represented by formula (5)

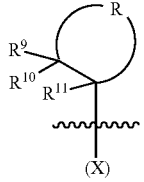
(5)

in the formula, R represents an alkylene group having 1 to 14 carbon atoms which optionally have a substituent; $R^9$, $R^{10}$ and $R^{11}$ independently represent a hydrogen atom, alkoxy group, aryloxy group, silyl group, amino group or hydrocarbon group having 1 to 30 carbon atoms which is optionally substituted by one or more groups selected from a halogen atom, alkoxy group and aryloxy group; at least one of $R^9$ and $R^{10}$ is not a hydrogen atom; $R^9$, $R^{10}$, $R^{11}$ and the above-mentioned alkylene group R optionally bond to each other to form a ring structure; in the formula, the bond of the carbon atom to X in formula (C1) is also shown;

Q represents a bivalent group indicated in the brackets of Z[—S(=O)$_2$—O-]M, Z[—C(=O)—O-]M, Z[—P(=O)(—OH)—O-]M or Z[—S-]M, wherein Z and M at the beginning and at the end of the formulae are described to show the coupling direction of the groups; Z represents a hydrogen atom or a hydrocarbon group having 1 to 40 carbon atoms which is optionally substituted by one or more groups selected from a halogen atom, alkoxy group and aryloxy group; Y and Z optionally bond to each other to form a ring structure; $R^6$ or $R^7$ optionally bond to Y to form a ring structure; L represents an electron-donating ligand and q is 0, ½, 1 or 2.

2. The method for producing a polymer as claimed in claim 1, wherein the copolymer is the copolymer of olefin represented by formula (1)

$$CH_2=CHR^1 \quad (1)$$

and a polar group-containing olefin represented by formula (2)

$$CH_2=CR^2R^3 \quad (2)$$

in the formula, $R^2$ represents a hydrogen atom or a methyl group; $R^3$ represents —COOR$^{12}$, —CN, —OCOR$^{12}$, —OR$^{12}$, —CH$_2$—OCOR$^{12}$, —CH$_2$OH, —CH$_2$—N(R$^{13}$)$_2$ or —CH$_2$-Hal, wherein $R^{12}$ represents a hydrogen atom or hydrocarbon group having 1 to 5 carbon atoms; $R^{13}$ represents a hydrogen atom, hydrocarbon group having 1 to 5 carbon atoms, aromatic substituent having 6 to 18 carbon atoms or alkoxy carbonyl group; and Hal represents a halogen atom.

3. The method for producing a polymer as claimed in claim 1, wherein the number of carbon atoms of the alkylene group R in formula (5) is 2 to 6.

4. The method for producing a polymer as claimed in claim 1, wherein the number of carbon atoms of the alkylene group R in formula (5) is 4.

5. The method for producing a polymer as claimed in claim 1, wherein at least one of $R^9$ and $R^{10}$ in formula (5) is an alkyl group having 1 to 6 carbon atoms or cycloalkyl group having 3 to 8 carbon atoms.

6. The method for producing a polymer as claimed in claim 1, wherein at least one of $R^9$ and $R^{10}$ in formula (5) is an isopropyl group.

7. The method for producing a polymer as claimed in claim 1, wherein at least one of $R^6$ and $R^7$ in formula (C1) is 2-isopropyl-5-methylcyclohexyl group (menthyl group) represented by the following formula

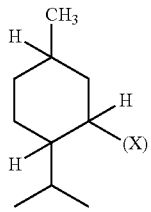

in the formula, the bond between the carbon atom and X is also shown and X has the same meaning as described in formula (C1).

8. The method for producing a polymer as claimed in claim 1, wherein both of $R^6$ and $R^7$ in formula (C1) are 2-isopropyl-5-methylcyclohexyl group (menthyl group).

9. The method for producing a polymer as claimed in claim 1, wherein the catalyst represented by formula (C1) is represented by formula (C2)

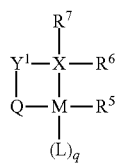

(C2)

in the formula, $Y^1$ represents a halogen atom or bivalent hydrocarbon group having 1 to 70 carbon atoms which is optionally substituted by one or more groups selected from alkoxy group and aryloxy group; Q, M, X, $R^5$, $R^6$, $R^7$, L and q have the same meaning as described in formula (C1).

10. The method for producing a polymer as claimed in claim 9, wherein Q in formula (C2) is —$SO_2$—O—, provided that S bonds to $Y^1$ and O bonds to M.

11. The method for producing a polymer as claimed in claim 9, wherein the catalyst represented by formula (C2) is represented by formula (C3)

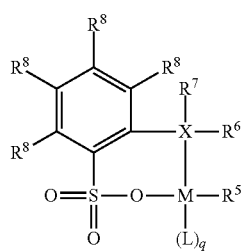

(C3)

in the formula, four $R^8$s independently represent a hydrogen atom, alkyl group having 1 to 8 carbon atoms, alkoxy group having 1 to 8 carbon atoms, aryloxy group having 6 to 18 carbon atoms or a halogen atom; and M, X, $R^5$, $R^6$, $R^7$, L and q have the same meanings as described in formula (C1).

12. The method for producing a polymer as claimed in claim 11, wherein all of $R^8$s in formula (C3) are a hydrogen atom.

13. The method for producing a polymer as claimed in claim 1, wherein M is Pd.

14. The method for producing a polymer as claimed in claim 1, wherein X is P.

15. The method for producing a polymer as claimed in claim 1, wherein the olefin represented by formula (1) is ethylene.

16. The method for producing a polymer as claimed in claim 1, wherein the polar group-containing olefin represented by formula (2) is an allyl compound in which $R^3$ represents —$CH_2$—$OCOR^{12}$, —$CH_2OH$, —$CH_2N$—$(R^{13})_2$ or —$CH_2$-Hal, wherein $R^{12}$, $R^{13}$ and Hal have the same meanings as described in formula (2).

17. The method for producing a polymer as claimed in claim 1, wherein the polar group-containing olefin represented by formula (2) is allyl acetate.

18. The method for producing a polymer as claimed in claim 10, wherein the catalyst represented by formula (C2) is represented by formula (C3)

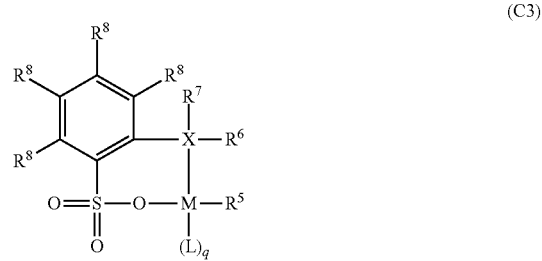

(C3)

in the formula, four $R^8$s independently represent a hydrogen atom, alkyl group having 1 to 8 carbon atoms, alkoxy group having 1 to 8 carbon atoms, aryloxy group having 6 to 18 carbon atoms or a halogen atom; and M, X, $R^5$, $R^6$, $R^7$, L and q have the same meanings as described in formula (C1).

19. The method for producing a polymer as claimed in claim 18, wherein all of $R^8$s in formula (C3) are a hydrogen atom.

* * * * *